United States Patent
Rubin et al.

(10) Patent No.: US 6,559,165 B1
(45) Date of Patent: May 6, 2003

(54) METHODS FOR TREATING BULIMIA USING OPTICALLY PURE (−) NORCISAPRIDE

(75) Inventors: Paul D. Rubin, Sudbury, MA (US); Timothy J. Barberich, Concord, MA (US)

(73) Assignee: Sepracor, Inc., Marlborough, MA (US)

(*) Notice: Subject to any disclaimer, the term of this patent is extended or adjusted under 35 U.S.C. 154(b) by 0 days.

(21) Appl. No.: 09/722,391

(22) Filed: Nov. 28, 2000

Related U.S. Application Data

(62) Division of application No. 09/332,195, filed on Jun. 14, 1999.
(60) Provisional application No. 60/122,236, filed on Mar. 1, 1999, and provisional application No. 60/089,225, filed on Jun. 15, 1998.

(51) Int. Cl.$^7$ ............................................. A61K 31/445
(52) U.S. Cl. ..................................................... 514/327
(58) Field of Search ......................................... 514/327

(56) References Cited

U.S. PATENT DOCUMENTS

| | | |
|---|---|---|
| 3,536,809 A | 10/1970 | Applezweig |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,598,123 A | 7/1986 | Cutter |
| 4,962,115 A | 10/1990 | Van Daele |
| 5,057,427 A | 10/1991 | Wald et al. |
| 5,057,525 A | 10/1991 | Van Daele |
| 5,059,595 A | 10/1991 | Le Grazie |
| 5,073,543 A | 12/1991 | Marshall et al. |
| 5,075,290 A | 12/1991 | Findley et al. |
| 5,077,217 A | 12/1991 | Matson et al. |
| 5,120,548 A | 6/1992 | McClelland et al. |
| 5,137,896 A | 8/1992 | Van Daele |
| 5,354,556 A | 10/1994 | Sparks et al. |
| 5,356,934 A | 10/1994 | Robertson et al. |
| 5,407,953 A | 4/1995 | Morgan |
| 5,422,374 A | 6/1995 | Miyao et al. |
| 5,502,067 A | 3/1996 | Morgan |
| 5,591,767 A | 1/1997 | Mohr et al. |
| 5,618,828 A | 4/1997 | Gray et al. |
| 5,629,328 A | 5/1997 | Gray et al. |
| 5,629,329 A | 5/1997 | Gray et al. |
| 5,639,476 A | 6/1997 | Oshlack et al. |
| 5,663,173 A | 9/1997 | Jegham et al. |
| 5,674,533 A | 10/1997 | Santus et al. |
| 5,712,293 A | 1/1998 | McCullough et al. |
| 5,733,566 A | 3/1998 | Lewis |
| 5,739,151 A | 4/1998 | McCullough et al. |
| 5,877,188 A | 3/1999 | McCullough et al. |
| 5,877,189 A | 3/1999 | McCullough et al. |
| 5,955,477 A | 9/1999 | Gray et al. |
| 5,955,478 A | 9/1999 | Gray et al. |
| 6,048,879 A | 4/2000 | Rubin et al. |
| 6,066,654 A | 5/2000 | Gray et al. |
| 6,069,154 A | 5/2000 | Gray et al. |
| 6,114,356 A | 9/2000 | McCullough et al. |

FOREIGN PATENT DOCUMENTS

| | | |
|---|---|---|
| EP | 0 076 530 A2 | 4/1983 |
| EP | 0 364 271 A1 | 4/1990 |
| FR | 0 748 807 A1 | 12/1996 |
| WO | 94/01111 | 1/1994 |
| WO | 94/01112 | 1/1994 |
| WO | 94/27599 | 12/1994 |
| WO | 95/01803 | 1/1995 |
| WO | 96/40133 | 12/1996 |
| WO | 98/03173 | 1/1998 |
| WO | 99/02496 | 1/1999 |

OTHER PUBLICATIONS

Crow, Exp. Opin. Invest. Drugs, 1997, 6(4), 427–436.*
Rissanen et al, J. Clin. Psychopharmacol., Feb. 1998, 18/1, 26–32.*
Ward R.M. et al., "Cisapride: A Survey of the Frequency of Use and Adverse Events in Premature Newborns", Pediatrics 103 (2):469–472 (1999).
Barnes, N.M. et al., "Identification of 5–HT3 Recognition Sites In The Ferret Area Postrema" J. Pharm. Pharmacol., 40:586–588 (1988).
Burks, T.F., *Principles of Pharmacology*, 1996, pps. 1093–1100.
Craig & Clark, "5–Hydroxytryptamine and Cholinergic Mechanisms in Guinea–pig Ileum," *Brit. J. Pharmacol.* 96:247 (1989).
Decktor, DL et al., "Effect of Metoclopramide, Bethanechol and the Cholecystokinin Receptor Antagonist, L–364, 718, on Gastric Emptying in the Rat," *Eur. J. Pharmacol.* 147:313–316 (1988).
Fernandez & Massingham, "Peripheral Receptor Populations Involved in the Regulation of Gastrointestinal Motility and the Pharmacological Actions of Meoclopramide–like Drugs," *Life Sci.* 36:1–14 (1985).
Frazer, A et al., "Subtypes of Receptors for Serotonin," *Annual Rev. of Pharamcology and Toxicology* 30:307–348 (1990).
Gladziwa, U et al., "Pharmacokinetics and pharmacodynamics of cisapride in patients undergoing hemodialysis," *Clinical Pharmacology* 50:6:673–681 (1991).
Gullikson, G.W., et al., "Relationship of Serotonin–3 Receptor Antagonist Activity to Gastric Emptying and Motor–Stimulating Actions of Prokinetic Drugs in Dogs," *J. Pharmacol. Experimen. Therp.*, 258(1):103–110 (1991).

(List continued on next page.)

Primary Examiner—Rebecca Cook
(74) Attorney, Agent, or Firm—Pennie & Edmonds LLP

(57) ABSTRACT

Methods for the prevention, treatment, or management of apnea, apnea disorders, bulimia nervosa, irritable bowel syndrome, urinary incontinence, bradycardia, bradyarrhythmia, syncope, other disorders, or symptoms thereof using (−) norcisapride, or a pharmaceutically acceptable salt thereof, substantially free of its (+) stereoisomer.

10 Claims, No Drawings

OTHER PUBLICATIONS

Jamali, F., "Enantioselective Aspects of Drug Action and Disposition: Therapeutic Pitfalls," *Journal of Pharmaceutical Sciences*, 78(9):695–715 (1989).

Krejs, GJ "Sérotonine intestinale, une cible thérapeutique," *Méd. Chir. Dig.* 22:7:415–416 (1993).

Lauwers, W et al., "Identification of a Biliary Metabolite of Cisapride," *Biomedical and Environmental Mass Spectrometry* 15:323–328 (1988).

Lavrijsen, K et al., "The Role of CYP3A4 in the In–Vitro Metabolism of Cisapride in Human Liver Microsomes and In–Vitro and In–Vivo Interactions of Cisapride with Co–Administered Drugs," *Dept. of Pharmacokinetics and Drug Metabolism*, Janssen Research Foundation.

Milo, R "Non–Cholinergic Non–antidopaminergic Treatment of Chronic Digestive Symptoms Suggestive Of A Motility Disorder A Two–Step Pilot Evaluation of Cisapride," *Curr. Therapeutic Research* 36:5:1053–1062 (1984).

Nemeth, P.R., "Gastrointestinal motility stimulating drugs and 5–HT receptors or Myenteric Neurons," *Eur. J. Pharmacol.*, 166:387–391 (1989).

Porsius, AJ et al., "Farmacotoets 6A," *Farmacotherapie* 129:9:214–217 (1994).

Preechagoon, Y. et al., "Analysis of Cisapride in Neonatal Plasma Using High–Performance Liquid Chromatography with a Base–Stable Column and Fluorescence Detection", *J. Chromatography B: Biomedical Applications*, 670(1):139–143 (1995).

Reyntjens, A et al., "Clinical Pharmacological Evidence For Cisapride's Lack of Antidopaminergic or Direct Cholinergic Properties," *Current Therapeutic Research* 36:5:1045–1052 (1984).

Schiavi, GB et al., "Identification of Serotonin 5–HT$_4$ Recognition Sites in the Porcine Caudate Nucleus by Radioligand Binding," *Neuropharmacology* 33:543–549 (1994).

Schuurkes, JAJ et al., "Motor–Stimulating Properties of Cisapride on Isolated Gastrointestinal Preparations of the Guinea Pig." *J. Pharmacol. Exp. Ther.* 234:775–783 (1985).

Stacher, G et al., "Effects of Oral Cisapride on Interdigestive Jejunal Motor Activity, Psychomotor Function, and Side–Effect Profile in Healthy Man," *Digestive Diseases and Sciences* 32:11:1223–1230 (1987).

Williams & Burks, "Cisapride Increases Gastric Emptying Without Affecting Small or Large Bowel Transit," *Proc. West. Pharmacol. Soc.* 28(47–50) (1985).

Zuccato, E et al., "The Effects of S(–) and R(+) Sulpride, Metoclopramide, Cisapride and Domperidone on the Small Intestine DA$_2$ –Receptors are Involved in the Control of Small Intestinal Transit Time in Rats," *Pharmacological Research* 26:2:179–185 (1992).

Messier, T. L., et al., "High Throughput Assays of Cloned Adrenergic, Muscarinic, Neurokinin, and Neurotrophin Receptors in Living Mammalian Cells," *Pharmacol. Toxicol.*, 76(5):308–311 (1995).

Burstein, E.S. et al., "Structure–Function of Muscarinic Receptor Coupling to G Proteins," *J. Biol. Chem.*, 270:3141–3146 (1995).

Faris, P.L. et al.,"Nociceptive, but not Tactile, Thresholds are Elevated in Bulimia Nervosa," *Biol. Psychiatry* 32:462–466 (1992).

Schapira, M. et al., "The Current Status of Gastric Prokinetic Drugs," *Acta Gastroenterolog. Belg.*, 53:446–457 (1990).

Dumuis, A. et al., "The Gastrointestinal Prokinetic Benzamide Derivatives are agonists at the non–classical 5–HT receptor (5–HT$_4$) Positively Coupled To Adenylate Cyclase In Neurons," *N.S. Arch Pharmacol.*, 340:403–410 (1989).

Clarke, D. E. et al., "The 5–HT$_4$ Receptor: Naughty, But Nice," *Trends in Pharmacological Sciences*, 10:385–386 (1999).

Blecker, U. et al., "The Role of "Occult" Gastroesophageal Reflux in Chronic Pulmonary Disease in Children," *Acta Gastro–Enterologica Belgica*, 58(5–6):348–352 (1995).

Shah, M., "Gastroesophageal Reflux—How to Mend it?" *Indian J. Pediatr.*, 63:441–445 (1996).

Skinner S., "Gastric Ulcer Presenting as Gastroesophageal Reflux and Apnea in a Term Neonate," *Tex. Medic.*, 94(9):57–58 (1998).

Noor, N. et al., XP002128489, "Effects of Cisapride on Symptoms and Postcibal Small–Bowel Motor Function in Patients with Irritable Bowel Syndrome", *Scandianavian J. Gastroent.*, 33(6)605–611 (1998).

Vandenplas Y., "Clinical Use of Cisapride and its Risk–benefit in Paediatric Patients," *Eur. J. Gastroent. Hepat.*, 10(10):871–881 (1998).

Meuldermans, W. et al., "Excretion and Biotransformatin of Cisapride In Dogs and Humans After Oral Administration," *Drug Metab. Dispos.*, 16(3): 403–409 (1988).

Costall B., et al., "Emesis Induced By Cisplatin In The Ferret As A Model For The Detection Of Anti–Emetic Drugs," *Neuropharmacology*, 26:1321–1326 (1987).

Meuldermans, W. et al., "Excretion and Biotransformatin of Cisapride in Rats After Oral Administration," *Drug Metab. Dispos.*, 16(3):410–419(1988).

Van Peer, A. et al., "Clinical Pharmacokinetics of Cisapride," *Excerpta Medica, Current Clinical Practice Series*, A.G. Johnson and G. Lux, Eds. Amsterdam, 48:23–29 (1988).

Van Daele, G.H. P. et al., "Synthesis of Cisapride, a Gastrointentestinal Stimulant Derived From Cis–4 – Amino–3–Methoxypiperidine," *Drug Development Res.*, 8:225–232 (1996).

Ebert, W. R., "Soft Elastic Gelatin Capsules: A Unique Dosage Form," *Pharm. Tech.*, 1(5):44–50 (1977).

\* cited by examiner

METHODS FOR TREATING BULIMIA USING OPTICALLY PURE (−) NORCISAPRIDE

This application is a division of U.S. application Ser. No. 09/332,195, filed Jun. 14, 1999, which claims priority to U.S. Provisional Application Nos. 60/089,225 and 60/122,236, filed Jun. 15, 1998 and Mar. 1, 1999, respectively.

FIELD OF THE INVENTION

The invention relates to methods of prevention, treatment, or management, of apnea, apnea disorders, bulimia, other disorders, or symptoms thereof.

BACKGROUND OF THE INVENTION

Apnea is defined in *Stedman's Medical Dictionary*, 26th Edition, Williams and Wilkins (1995), as the absence of breathing. There are a number of disorders associated with apnea, which are characterized by interrupted breathing in which a person stops breathing long enough to decrease the amount of oxygen and increase the amount of carbon dioxide in the blood and brain. Each type of apnea involves the absence of airflow at the nose or the mouth, typically for at least 10 seconds.

Various apnea disorders exist, including: central apnea, which results from medullary depression and inhibits respiratory movement; deglutition apnea, which is the inhibition of breathing during swallowing; obstructive or peripheral apnea, which is either a result of obstruction of air passages or inadequate respiratory muscle activity; sleep apnea, which is central and/or obstructive apnea during sleep; and sleep induced apnea, which results from failure of the respiratory center to stimulate adequate respiration during sleep.

Obstructive apneas usually occur in obese men and are much less common in women. The obesity, perhaps in combination with aging body tissues and other factors, leads to narrowing of the upper airways. Tobacco smoking, excessive alcohol use, and lung diseases, such as emphysema, increase the risk of developing obstructive apneas.

For those suffering from sleep apnea, quitting smoking, avoiding excessive use of alcohol, and losing weight are commonly the first behavioral steps for treating the disorder. In order to inhibit or avoid apnea, heavy snorers and people who often choke in their sleep should not take tranquilizers, sleep aids, or other sedating drugs.

Sleep apnea is one of the most common forms of apnea. Rarely, a person who has severe sleep apnea needs a tracheostomy, a surgical procedure that creates a permanent opening into the windpipe through the neck. Sometimes other surgical procedures are performed to widen the upper airway and alleviate the problem. However, such extreme measures are seldom needed and never desired.

Apnea can also be treated by non-invasive means by administering to a patient a therapeutic agent. U.S. Pat. No. 5,075,290 discloses the medical treatment of obstructive sleep apnea and associated symptoms, such as snoring, by the administration of the nucleoside uptake blocker, dipyridamole, during sleep. U.S. Pat. Nos. 5,502,067 and 5,407,953 disclose a method of treating sleep apnea, hyponea and snoring in a human patient by administering a pilocarpine compound. U.S. Pat. No. 5,422,374 discloses a method of treating sleep apnea by the administration of ubidecarenone to a patient. U.S. Pat. No. 5,356,934 discloses a method of employing (R)-fluoxetine to treat sleep apnea.

Bulimia nervosa, or bulimia, is a disorder described in the *Diagnostic and Statistical Manual of Mental Disorders*, Fourth Edition, American Psychiatric Association, 1996 ("DSM-IV"), which is characterized in part by recurrent episodes of binge eating during which the patient experiences a loss of control resulting in over eating and self-induced vomiting. The disorder primarily afflicts females of upper and middle socioeconomic status, especially college-age women.

Currently, two approaches for treating bulimia are used: cognitive-behavioral and pharmacological. Traditional pharmacological treatments involved antidepressants. More recent research into the fundamental causes of bulimia, however, has suggested other pharmacological treatments. In particular, some researchers have argued that the pathophysiological characteristics driving the behaviors characteristic of bulimia involve an increase in the basal tone of the vagal nerve, and have suggested that racemic ondansetron may be useful for the treatment of bulimia Faris, P. L. et al., *Biol. Psychiatry*, 32:462–466 (1992); Dumuis et al., *N. S. Arch. Pharmacol.*, 340:403–410 (1989).

Cisapride, chemically named cis-4-amino-5-chloro-N-[1-[3-(4-fluorophenoxy)propyl]-3-methoxy-4-piperidinyl]-2-methoxybenzamide, is a benzamide derivative, the parent compound being metoclopramide. Schapira et al., *Acta Gastroenterolog. Belg.*, LIII:446–457 (1990). Benzamide derivatives have several prominent pharmacological actions due to their effects on neuronal systems modulated by the neurotransmitter serotonin.

Because of their modulation of the serotonin neuronal system in the gastrointestinal tract, many benzamide derivatives are effective antiemetic agents and are commonly used to control vomiting during cancer chemotherapy or radiotherapy. Costall et al., *Neuropharmacology*, 26:1321–1326 (1987). This action is almost certainly the result of an ability to block serotonin at specific sites, particularly type-3 5-hydroxytryptamine (5-HT$_3$) receptors. Clarke et al., *Trends in Pharmacological Sciences*, 10:385–386 (1989). In theory, chemotherapy and radiation therapy can induce nausea and vomiting by damaging enterochromaffin cells in the gastrointestinal tract. As a result, the neurotransmitter serotonin is released and stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved. Barnes et al., *J. Pharm. Pharmacol.*, 40:586–588 (1988).

Racemic cisapride is used primarily to treat gastroesophageal reflux disease ("GERD"), which is characterized as the backward flow of the stomach contents into the esophagus. Cisapride is commercially available as the racemic mixture of the cis diastereomeric enantiomers of cisapride known as PROPULSID®.

The co-administration of racemic cisapride with other therapeutic agents causes inhibitory problems with the metabolism of cisapride by the liver. For example, ketoconazole has a pronounced effect on cisapride kinetics resulting from the inhibition of the metabolic elimination of cisapride and leads to an 8-fold increase of the steady-state plasma levels. *Physician's Desk Reference®*, 52nd Edition, Medical Economics Co., Inc., 1998. Interaction of racemic cisapride and other therapeutic agents can also potentiate cardiovascular side effects, such as cardiotoxicity. This potentiation occurs when other drugs present in the patient's system interfere with the metabolism of cisapride, thereby building up racemic cisapride in the body.

These interactions are a significant drawback to the use of racemic cisapride; in particular, because racemic cisapride is often used before, with or immediately after another therapeutic agent. In addition, administration of racemic cisapride to a human has been found to cause adverse effects such as cardiac arrhythmia, including ventricular tachycardia, ventricular fibrillation, $Q_T$ prolongation, and torsades de pointes, central nervous system ("CNS") effects, increased systolic pressure, interactions with other drugs, diarrhea, abdominal cramping and cardiac depression.

Racemic cisapride is almost completely absorbed after oral administration to humans, but bioavailability of cisapride is only 40–50% due to rapid first-pass metabolism in the liver. Van Peer et al., in *Progress in the Treatment of Gastrointestinal Motility Disorders: The Role of Cisapride,* Proceedings of a Symposium in Frankfurt, Germany, November 1986, Excerpta Medica, A. G. Johnson and G Lux Eds., Amsterdam, pp. 23–29 (1988). More than 90% of a dose of racemic cisapride in humans is metabolized mainly by oxidative N-dealkylation of the piperidine nitrogen or by aromatic hydroxylation occurring on either the 4-fluorophenoxy or benzamide rings. Meuldermans et al., *Drug Metab. Dispos.,* 16(3):410–419 (1988); and Meuldermans et al., *Drug Metab. Dispos.,* 16(3):403–409 (1988). Norcisapride, chemically named 4-amino-5-chloro-N-(3-methoxy-4-piperidinyl)-2-methoxybenzamide, is a metabolite of cisapride.

Recently, investigators have reported that the optically pure (–) stereoisomer of the cisapride metabolite norcisapride exhibits many of the useful characteristics, but without certain of the attendant side effects of racemic cisapride. U.S. Pat. No. 5,712,293 discloses methods of treating gastroesophageal reflux disease, and other conditions, including emesis, dyspepsia, constipation, gastroparesis, intestinal pseudo-obstruction, and postoperative ileus using (–) norcisapride.

It is desirable to provide safe and effective methods of preventing, treating, or managing apnea, apnea disorders, bulimia nervosa and related disorders, or symptoms thereof, particularly a treatment that allows the patient to undergo other related therapies without adverse effects or drug-drug interactions.

SUMMARY OF THE INVENTION

The present invention encompasses the use of the optically pure (–) norcisapride, or a pharmaceutically acceptable salt thereof, substantially free of its (+) stereoisomer, in preventing, treating, or managing apnea, apnea disorders, bulimia, irritable bowel syndrome, asthma, urinary incontinence, syncope, bradycardia, bradyarrhythmia, or symptoms thereof. It should be understood that the invention encompasses any combination of preventing, treating, or managing each disorder or multiple disorders.

This invention also relates to pharmaceutical compositions adapted for the prevention, treatment, or management of a patient suffering from a vagal nerve mediated disorder or symptoms thereof, which comprises a therapeutically effective amount of (–) norcisapride, or a pharmaceutically acceptable salt thereof, substantially free of its (+) stereoisomer.

This invention also relates to pharmaceutical compositions adapted for the prevention, treatment, or management of a patient suffering from apnea, apnea disorders, or symptoms thereof, which comprises a therapeutically effective amount of (–) norcisapride, or a pharmaceutically acceptable salt thereof, substantially free of its (+) stereoisomer.

This invention further relates to pharmaceutical compositions adapted for the prevention, treatment, or management of bulimia, irritable bowel syndrome, asthma, urinary incontinence, bradycardia, bradyarrhythmia, syncope, related disorders, and symptoms thereof in a mammal, which comprises a therapeutically effective amount of (–) norcisapride, or a pharmaceutically acceptable salt thereof, substantially free of its (+) stereoisomer, said amount being sufficient to alleviate symptoms of said conditions while reducing or avoiding adverse effects associated with administration of racemic cisapride.

The invention also encompasses single unit dosage forms of optically pure (–) norcisapride, or a pharmaceutically acceptable salt thereof, substantially free of its (+) stereoisomer, which comprise from about 0.5 mg to about 500 mg of active ingredient in a compressed tablet. This dosage form is particularly suitable for the prevention, treatment, or management of apnea, apnea disorders, bulimia, irritable bowel syndrome, asthma, urinary incontinence, bradycardia, bradyarrhythmia, syncope, related disorders, or symptoms thereof.

DETAILED DESCRIPTION OF THE INVENTION

The present invention encompasses the use of optically pure (–) norcisapride, or a pharmaceutically acceptable salt thereof, substantially free of its (+) stereoisomer, in preventing, treating, or managing disorders, including, but not limited to, apnea, apnea disorders, bulimia, irritable bowel syndrome, asthma, urinary incontinence, bradycardia, bradyarrhythmia, syncope, and related disorders, or symptoms thereof. Apnea or apnea disorders include, but are not limited to, central apnea, deglutition apnea, obstructive or peripheral apnea, sleep apnea, and sleep induced apnea, or a combination thereof.

The present invention also encompasses the use of optically pure (–) norcisapride, or a pharmaceutically acceptable salt thereof substantially free of its (+) stereoisomer, in preventing, treating, or managing apnea, apnea disorders, bulimia, irritable bowel syndrome, asthma, urinary incontinence, bradycardia, bradyarrhythmia, syncope, and related disorders, or symptoms thereof, preferably while reducing or avoiding adverse effects associated with administration of racemic cisapride.

In one embodiment, the present invention relates to a method of preventing, treating, or managing bulimia comprising administering to a patient a therapeutically effective amount of (–) norcisapride, or a pharmaceutically acceptable salt thereof, substantially free of its (+) stereoisomer.

In another embodiment, the present invention relates to a method of preventing, treating, or managing apnea or apnea disorders comprising administering to a patient a therapeutically effective amount of (–) norcisapride, or a pharmaceutically acceptable salt thereof, substantially free of its (+) stereoisomer.

In another embodiment, the present invention relates to a method for preventing, treating, or managing conditions mediated by vagal activity in a patient comprising administering a therapeutically effective amount of (–) norcisapride, or a pharmaceutically acceptable salt thereof, substantially free of its (+) stereoisomer.

The present invention also encompasses a method of preventing, treating, or managing irritable bowel syndrome comprising administering to a patient a therapeutically effective amount of (−) norcisapride, or a pharmaceutically acceptable salt thereof, substantially free of its (+) stereoisomer.

In another embodiment, the present invention relates to methods of preventing, treating, or managing syncope, and in particular vasovagal syncope and cardiac or carotid sinus syncope, which comprises administering to a patient a therapeutically effective amount of (−) norcisapride, or a pharmaceutically acceptable salt thereof, substantially free of its (+) stereoisomer.

The present invention further encompasses methods of preventing, treating, or managing bradycardia or bradyarrhythmia, which comprises administering to a patient a therapeutically effective amount of (−) norcisapride, or a pharmaceutically acceptable salt thereof, substantially free of its (+) stereoisomer.

In another embodiment, the present invention relates to a method of preventing, treating, or managing asthma or asthma symptoms, which comprises administering to a patient a therapeutically effective amount of (−) norcisapride, or a pharmaceutically acceptable salt thereof, substantially free of its (+) stereoisomer.

The present invention also encompasses a method of preventing, treating, or managing urinary incontinence, which comprises ad ministering to a patient a therapeutically effective amount of (−) norcisapride, or a pharmaceutically acceptable salt thereof, substantially free of its (+) stereoisomer.

In another embodiment, this invention encompasses single unit dosage forms of (−) norcisapride, or a pharmaceutically acceptable salt thereof, substantially free of its (+) stereoisomer, which comprise from about 0.5 mg to about 500 mg of active ingredient in a compressed tablet. This dosage form is particularly suitable for the prevention, treatment, or management of apnea, apnea disorders, bulimia, irritable bowel syndrome, asthma, urinary incontinence, bradycardia, bradyarrhythmia, syncope, related disorders, or symptoms thereof.

The vagus nerve is the largest nerve of the cranial nerves. There are two main branches of the vagus nerve, each of which act to provide both motor and sensory functions. The vagus nerves contain efferent fibers, which carry impulses from the nerve's origin in the medulla obligata of the brain to a tissue or visceral organ, and afferent fibers, which carry impulses from the organ back to the brain. It is present in a large portion of the body, extending from the brain stem to the organs of the neck, chest, and abdomen. Vagal stimulation occurs in a number of organs, including the heart, lungs, bronchia, trachea, esophagus, stomach, pancreas, small intestine, large intestine, colon, liver, gall bladder, and portions of the urinary tract.

Without being limited by theory, it is believed that symptoms of bulimia, irritable bowel syndrome, urinary incontinence, bradycardia, bradyarrhythmia, asthma, and syncope, particularly vasovagal syncope and cardiac or carotid sinus syncope, are affected by the basal tone of the vagus, or vagal, nerve.

Without being limited by theory, it is further believed that by blocking 5-HT-induced depolarization in the vagus, or vagal, nerve, (−) norcisapride lessens or inhibits symptoms of these disorders. Therefore, in one embodiment, the present invention relates to the use of optically pure (−) norcisapride, or a pharmaceutically acceptable salt thereof, substantially free of its (+) stereoisomer, in preventing, treating, or managing bulimia, irritable bowel syndrome, asthma, urinary incontinence, bradycardia, bradyarrhythmia, syncope, and related disorders, or symptoms thereof.

Additionally, the invention includes the use of (−) norcisapride, or a pharmaceutically acceptable salt thereof, substantially free of its (+) stereoisomer, in combination with other therapeutic agents. Examples of other therapeutic agents include, but are not limited to, fluoxetine or the R or S stereoisomer thereof; descarboethoxyloratidine; ondansetron or the R or S stereoisomer thereof, preferably R ondansetron; ubidecarenone; dipyridarnole; pilocarpine or the stereoisomers thereof; primidone or the R or S stereoisomer thereof; orphenadrine citrate; and the like, as well as any active metabolites thereof Administration of (−) norcisapride, or a pharmaceutically acceptable salt thereof, substantially free of its (+) stereoisomer, in combination with these other therapeutic agents for the prevention, treatment, or management of apnea, apnea disorders, bulimia, irritable bowel syndrome, urinary incontinence, bradycardia, bradyarrhythmia, asthma, syncope, or symptoms thereof in the methods of the present invention, may be made either concurrently or sequentially, i.e., (−) norcisapride and at least one other therapeutic agent may be administered as a combination, concurrently but separately, or by sequential administration. The compositions administered in each of these methods may be concurrent, sequential, or in any combination of concurrent or sequential.

The methods and compositions of this invention also include the benefit of reducing or avoiding adverse effects associated with administration of racemic cisapride. The invention also allows the concurrent or sequential use of antidepressant drugs, such as tricyclic antidepressants, fluoxetine or its R or S stereoisomer, Zoloft®, and the like, and other drugs, such as anti-anxiety drugs.

The term "patient" as used herein refers to mammals, particularly humans.

The methods of the present invention for the prevention, treatment, or management of bulimia are particularly useful in adolescents and young adults. In a preferred embodiment, the method of preventing, treating, or managing bulimia is directed to females from the ages of 13 to 25. It should be recognized that the methods of the present invention can be used to prevent, treat, or manage bulimia in males and females, including children and adults, notwithstanding the preferences mentioned above.

The methods of the present invention for the prevention, treatment, or management of apnea or apnea disorders are particularly useful in obese men. In a preferred embodiment, the methods are directed to the prevention, treatment, or management of obstructive apnea in obese men. It should be recognized that the methods can be used to prevent, treat, or manage apnea or apnea disorders in males and females, including children and adults, notwithstanding the preferences mentioned above.

As used herein, the terms "adverse effects" and "adverse side effects" include, but are not limited to, cardiac arrhythmia, cardiac conduction disturbances, appetite stimulation, weight gain, sedation, gastrointestinal distress, headache, dry mouth, constipation, diarrhea, and drug-drug interactions. See, for example, *Physician's Desk Reference®*, 52$^{nd}$ Edition, Medical Economics Co., Inc., pp. 1308–1309, 1998. The term "cardiac arrhythmia" includes, but is not limited to, ventricular tachyrhythmia, torsades de pointes, $Q_T$ prolongation, and ventricular fibrillation.

The term "racemic" as used herein means a mixture of the (−) and (+) enantiomers of a compound wherein the (−) and (+) enantiomers are present in approximately a 1:1 ratio.

The terms "substantially optically pure," "optically pure," and "optically pure enantiomers," as used herein, mean that the composition contains greater than about 90% of the (−) norcisapride stereoisomer by weight, preferably greater than about 95% of the desired enantiomer by weight, and more preferably greater than about 99% of the desired enantiomer by weight, based upon the total weight of norcisapride. In other words, the term "substantially free" means less than about 10 weight percent, preferably less than about 5 weight percent, and more preferably less than about 1 weight percent of (+) norcisapride is present according to the invention.

The terms "5-hydroxytryptamine receptor antagonist," "serotonin receptor antagonist," and "5-HT$_3$ receptor antagonist," as used herein, mean a compound capable of binding reversibly to a 5-hydroxytryptamine receptor, whether on the vagal nerve or elsewhere in a mammal.

The phrases "bulimia" and "bulimia nervosa" are used herein consistently with the definition according to DSM-IV.

The terms "apnea" and "apnea disorder," as used herein, include, but are not limited to, a disorder characterized by interrupted breathing, in which a person stops breathing long enough to decrease the amount of oxygen and increase the amount of carbon dioxide in the blood and brain.

The term "asthma," as used herein, is defined as a disorder characterized by increased responsiveness of the trachea and bronchi to various stimuli which results in symptoms that include, but are not limited to, wheezing, cough, shortness of breath, dyspnea, and the like. Asthma includes, for example, allergic asthma.

The term "syncope," as used herein, is defined as a disorder characterized by loss of consciousness and postural tone caused by diminished cerebral blood flow. Syncope includes, for example, Adams-Stokes syncope, cardiac syncope, carotid sinus syncope, hysterical syncope, laryngeal syncope, local syncope, micturition syncope, orthostatic syncope, postural syncope, swallow syncope, syncope due to seizures, syncope due to pulmonary embolism, syncope of gradual onset, tussive syncope, vasodepressor syncope, or vasovagal syncope.

The phrase "therapeutically effective amount of (−) norcisapride," as used herein, means that amount of substantially optically pure (−) norcisapride, or a pharmaceutically acceptable salt thereof, which, alone or in combination with other drugs, provides a therapeutic benefit in the prevention, treatment, or management, or of apnea, apnea disorders, bulimia, irritable bowel syndrome, urinary incontinence, bradycardia, bradyarrhythmia, asthma, syncope, or one or more symptoms thereof. Different therapeutically effective amounts may be applicable for each disorder, as will be readily known by those of ordinary skill in the art.

Substantially pure (−) norcisapride may be obtained from a racemic mixture of cisapride, the chemical synthesis of which can be performed according to the method described in European Patent Application No. 0,076,530 A2 published Apr. 13, 1983, U.S. Pat. Nos. 4,962,115, 5,057,525, 5,137,896, the disclosures of which are each hereby incorporated herein by express reference thereto. See also, and Van Daele, et al., *Drug Development Res.,* 8:225–232 (1986). The metabolism of cisapride to norcisapride is described in Meuldermans, W., et al., *Drug Metab. Dispos.,* 16(3): 410–419 (1988) and Meuldermans, W., et al., *Drug Metab. Dispos.,* 16(3):403–409 (1988). The preparation of racemic norcisapride is also known to those of ordinary skill in the art, particularly in view of EP 0,076,530 A2 and U.S. Pat. No. 5,137,896 to Van Daele, the disclosures of which are hereby incorporated herein by express reference thereto.

Optically pure (−) norcisapride may also be obtained from racemic norcisapride by HPLC separation or resolution of the enantiomers using conventional means, for example, from an optically active resolving acid. The resolution of racemic norcisapride is also known to those of ordinary skill in the art, particularly from Jacques, J., et al., *Enantiomers, Racemates and Resolutions* (Wiley-Interscience, New York, 1981); Wilen, S. H., et al., *Tetrahedron,* 33:2725 (1977); Eliel, E. L. *Stereochemistry of Carbon Compounds* (McGraw-Hill, N.Y., 1962); Wilen, S. H. *Tables of Resolving Agents and Optical Resolutions,* p. 268 (E. L. Eliel, Ed. Univ. of Notre Dame Press, Notre Dame, Id., 1972).

In addition to separation techniques, such as those described above, (−) norcisapride may be synthesized by stereospecific synthesis using methodology well known to those of ordinary skill in the art. Chiral synthesis can result in products of high enantiomeric purity. However, in some cases, the enantiomeric purity of the product is not sufficiently high. The skilled artisan will appreciate that the separation methods described above may be used to further enhance the enantiomeric purity of (−) norcisapride obtained by chiral synthesis.

Optically pure (−) norcisapride may also be prepared from the racemic mixture by enzymatic biocatalytic resolution. See, for example, U.S. Pat. Nos. 5,057,427 and 5,077,217, the disclosures of which are incorporated herein by express reference thereto.

The magnitude of a prophylactic or therapeutic dose of (−) norcisapride, or a pharmaceutically acceptable salt thereof, substantially free of its (+) stereoisomer, in the acute or chronic management of diseases and disorders described herein will vary with the severity of the condition to be prevented, treated, or managed and the route of administration. For example, oral, mucosal (including rectal), parenteral (including subcutaneous, intramuscular, bolus injection, and intravenous), sublingual, transdermal, nasal, buccal, and like may be employed. Dosage forms include tablets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those skilled in the art with due consideration of such factors. In general, the total daily dosage for the conditions described herein, is from about 0.5 mg to about 500 mg of (−) norcisapride, or a pharmaceutically acceptable salt thereof, substantially free of its (+) stereoisomer. Preferably, a daily dose range is from about 1 mg to about 250 mg and more preferably, a daily dose range is between about 1 mg to about 100 mg. Preferably, the active ingredient is administered in single or divided doses orally from one to four times a day, or by slow intravenous injection. The most preferred route of administration for the present invention is oral. The oral dosage forms may be conveniently presented in unit dosage forms and prepared by any methods well known in the art of pharmacy.

In managing the patient, the therapy may be initiated at a lower dose, e.g., from about 0.5 mg to about 10 mg, and increased up to the recommended daily dose or higher depending on the patient's global response. It is further recommended that children, patients over 65 years, and those with impaired renal or hepatic function, initially receive low doses, and that they be titrated based on individual response(s) and blood level(s). It may be necessary to use dosages outside these ranges in some cases, as will be apparent to those of ordinary skill in the art. Furthermore, it is noted that the clinician or treating physician will know how and when to interrupt, adjust, or terminate therapy in conjunction with individual patient response.

Any suitable route of administration may be employed for providing the patient with an effective dosage of (−) norcisapride, or a pharmaceutically acceptable salt thereof, substantially free of its (+) stereoisomer. The most suitable route in any given case will depend on the nature and severity of the condition being prevented, treated, or managed.

The pharmaceutical compositions for use in the present invention comprise optically pure (−) norcisapride, or a pharmaceutically acceptable salt thereof, substantially free of its (+) stereoisomer, as the active ingredient, and may also contain a pharmaceutically acceptable carrier, and optionally, other therapeutic ingredients. As used herein, the term "pharmaceutically acceptable salt" refers to a salt prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), med ianesulfonic, ethanesulfonic, pantothenic, benzenesulfonic (besylate), stearic, sulfanilic, alginic, galacturonic, and the like. Particularly preferred acids are hydrobromic, hydrochloric, phosphoric, and sulfuric acids. In a preferred embodiment, (−) norcisapride is administered as the free base or hydrate.

In practical use, (−) norcisapride, or a pharmaceutically acceptable salt thereof, substantially free of its (+) stereoisomer, can be combined as the active ingredient in intimate admixture with a pharmaceutical carrier according to conventional pharmaceutical compounding techniques. The carrier may take a wide variety of forms and may comprise a number of components depending on the form of preparation desired for administration. The compositions of the present invention include, but are not limited to, suspensions, solutions and elixirs; aerosols; or carriers, including, but not limited to, starches, sugars, microcrystalline cellulose, diluents, granulating agents, lubricants, binders, disintegrating agents, and the like. Because of their ease of administration, tablets and capsules are preferred and represent the most advantageous oral dosage unit form, in which case solid pharmaceutical carriers are employed. If desired, tablets may be coated by standard aqueous or nonaqueous techniques.

Pharmaceutical compositions of the present invention suitable for oral administration may be presented as discrete pharmaceutical unit dosage forms, such as capsules, cachets, soft elastic gelatin capsules, tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the pharmaceutically acceptable carrier which constitutes one or more necessary ingredients. In general, the compositions are prepared by uniformly and intimately admixing the active ingredient with liquid carriers or finely divided solid carriers or both, and then, if necessary, shaping the product into the desired presentation. Oral solid preparations are preferred over oral liquid preparations. One preferred oral solid preparation is capsules, but the most preferred oral solid preparation is tablets.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, granulating agent, surface active agent, dispersing agent, or the like. Molded tablets may be made by molding, in a suitable machine, a mixture of the powdered compound moistened with an inert liquid diluent. Preferably, each tablet contains from about 0.5 mg to about 500 mg of the active ingredient, more preferably from about 1 mg to about 250 mg. Preferably, each cachet or capsule contains from about 0.5 mg to about 500 mg of the active ingredient, more preferably from about 1 mg to about 250 mg. However, the amount of active ingredient found in the composition may vary depending on the amount of active ingredient to be administered to the patient.

Optically pure (−) norcisapride, or a pharmaceutically acceptable salt thereof, substantially free of its (+) stereoisomer, may be formulated as a pharmaceutical composition in a soft elastic gelatin capsule unit dosage form by using conventional methods well known in the art, such as in Ebert, *Pharm. Tech,* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof.

In addition to the common dosage forms set out above, the compounds of the present invention may also be administered by controlled release means, delivery devices, or both, as are well known to those of ordinary skill in the art, such as those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations known to those of ordinary skill in the art, including those described herein, may be readily selected for use with the (−) norcisapride compositions of the invention. Thus, single unit dosage forms suitable for oral administration, such as tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradual and continual release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of the active ingredient may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., (−) norcisapride) in the pharmaceutical composition.

Optically pure (−) norcisapride, or a pharmaceutically acceptable salt thereof, substantially free of its (+) stereoisomer, may also be formulated for parenteral administration by injection (subcutaneous, bolus injection, intramuscular, or intravenous), and may be dispensed in a unit dosage form, such as a multidose container or an ampule. Compositions of (−) norcisapride, or a pharmaceutically acceptable salt thereof, substantially free of its (+) stereoisomer, for parenteral administration may be in the form of suspensions, solutions, emulsions, or the like in aqueous or oily vehicles, and in addition to the active ingredient may contain one or more formulary agents, such as dispersing agents, suspending agents, stabilizing agents, preservatives, and the like.

In the case where an intravenous injection or infusion composition is employed, a suitable daily dosage range is, e.g., from about 0.5 mg to about 500 mg total daily dose, preferably from about 1 mg to about 250 mg, more preferably from about 1 mg to about 100 mg.

Another preferred route of administration is transdermal delivery, for example, via an abdominal skin patch.

The invention is further defined by reference to the following examples, describing in detail the preparation of the compound and the compositions of the present invention, as well as their utility. It will be apparent to those skilled in the art that many modifications, both to materials and methods, may be practiced without departing from the purpose and interest of this invention.

EXAMPLES

Example 1

Bioavailability

A single dose of test substance or vehicle is administered to male beagle dogs either intravenously as a bolus over one minute using a 23 gauge butterfly needle into the saphenous vein, or as a single dose via oral gavage. 2.0 mL of whole blood is collected from each dog prior to and at intervals of 0.083, 0.25, 0.5, 1, 2, 3, 4, 6, 9, 12, and 24 hours following the intravenous or oral administration of the optical isomers or racemic mixture of cisapride or of norcisapride. The dogs are placed in sling-restraint prior to administration of test substance and are transferred to metabolic cages following collection of the 0.083 hour blood sample. All blood samples are collected from an angiocatheter placed in a cephalic vein on the morning of the experiment.

The blood is drawn into a 3 cc syringe. The first 1.0–2.0 mL of blood is discarded. The next 2.0 mL of whole blood is quickly transferred to a heparinized tube. The heparinized tubes are kept on ice until the blood is added. After adding the blood to the tube, the contents of the tube are mixed and centrifuged to obtain plasma. The plasma is carefully decanted and transferred to a test tube labeled with: the animal number, the dose of test substance administered, the route of administration, the date of administration, and the time of blood collection. The tubes are stored at −20° C. until analysis.

Analysis of the concentration of the optical isomers or racemates of norcisapride in each plasma sample is determined using high performance liquid chromatography. For each test substance the plasma concentration with respect to sample time is plotted for both routes of administration. The oral bioavailability of each test substance is determined by comparing the $C_{max}$ and AUC for the oral route of administration versus those for the intravenous route. The $t_{4/3}$ for each test substance by both routes is calculated as an indicator of duration of action.

Example 2

Receptor Activity

5-$HT_{1A}$ Receptor Activity

Receptor selection and amplification technology (R-SAT) is used (Receptor Technologies Inc., Winooski, Vt.) to determine potential agonist and/or antagonist activity of racemic norcisapride, cisapride, and their enantiomers on cloned human serotonin [5]-$HT_{1A}$ receptor subtypes expressed in NIH 3T3 cells, such as in Burstein el al., *J. Biol Chem.*, 270:3141–3146 (1995); and Messier et al., *Pharmacol. Toxicol.*, 76(5):308–311 (1995).

The assay involves co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells are incubated, plated, and then transfected using human 5-$HT_{1A}$ serotonin receptors, pSV-β-galactosidase, and salmon sperm DNA. The medium is changed one day later, and after 2 days, aliquots of the trypsinized cells are placed in wells of a 96 well plate. After five days in culture in the presence of the ligands, the levels of β-galactosidase are measured. The cells are then rinsed and incubated with the substrate, o-nitrophenyl β-D-galactopyranoside. After 16 hours, the plates are read at 405 nm on a plate-reader. Each compound is tested for activity in triplicate at seven different concentrations (10, 2.5, 0.625, 0.156, 0.039, 0.0098, and 0.0024 nM).

None of the compounds tested show agonist activity at human 5-$HT_{1A}$ serotonin receptors. Data from antagonist inhibition of the compounds are fit to the equation:

$$\text{Response} = \text{Max Response} + \frac{(\text{Min Response})}{1 + (\text{Ligand Conc}/EC_{50})}$$

$IC_{50}$ values (concentration required to inhibit 50% of specific binding) are calculated for antagonist activity against a concentration of 2 μM 5-HT using the non-linear least squares analysis of KaleidaGraph, the results of which are set forth in Tables 1 and 2.

5-HT$_2$ Receptor Activity

Receptor selection and amplification technology (R-SAT) is used (Receptor Technologies Inc., Winooski, Vt.) to determine potential agonist and/or antagonist activity of racemic norcisapride, cisapride, and their enantiomers on cloned human serotonin 5-HT$_2$ receptor subtypes expressed in NIH 3T3 cells, such as in Burstein et al., *J. Biol. Chem.*, 270:3141–3146 (1995); and Messier et al., *Pharmacol. Toxicol.*, 76(5):308–311 (1995).

The assay involves co-expression of a marker enzyme, β-galactosidase, with the serotonin receptor of interest. Ligands stimulate proliferation of cells that express the receptor and, therefore, the marker. Ligand-induced effects can be determined by assay of the marker.

NIH 3T3 cells are incubated, plated, and then transfected using human 5-HT$_2$ serotonin receptors, pSV-β-galactosidase, and salmon sperm DNA. The medium is changed one day later, and after 2 days, aliquots of the trypsinized cells are placed in wells of a 96 well plate. After five days in culture in the presence of the ligands, the levels of β-galactosidase are measured. The cells are then rinsed and incubated with the substrate, o-nitrophenyl β-D-galactopyranoside. After 16 hours, the plates are read at 405 nm on a plate-reader. Each compound is tested for activity in triplicate at seven different concentrations (10, 2.5, 0.625, 0.156, 0.039, 0.0098, and 0.0024 nM).

None of the compounds tested show agonist activity at human 5-HT$_2$ serotonin receptors. Data from antagonist inhibition of the compounds are fit to the equation:

$$\text{Response} = \text{Max Response} + \frac{(\text{Min Response})}{1 + (\text{Ligand Conc}/EC_{50})}$$

IC$_{50}$ values are calculated for antagonist activity against a concentration of 2 μM 5-HT using the non-linear least squares analysis of KaleidaGraph, the results of which are set forth in Tables 1 and 2.

TABLE 1

Calculated IC$_{50}$ Values (μM) at 5-HT$_{1A}$ and 5-HT$_2$ Receptors

| Compound | 5-HT$_{1A}$ | 5-HT$_2$ |
| --- | --- | --- |
| (±) Norcisapride | 7.48 | 2.21 |
| (+) Norcisapride | 0.0054 | 0.38 |
| (−) Norcisapride | 1.30 | — |

TABLE 2

Calculated IC$_{50}$ Values (μM) at 5-HT$_{1A}$ and 5-HT$_2$ Receptors

| Compound | 5-HT$_{1A}$ | 5-HT$_2$ |
| --- | --- | --- |
| (±) Cisapride | — | 0.26 |
| (+) Cisapride | — | 0.0050 |
| (−) Cisapride | — | 7.08 |

Example 3
Receptor Binding

5-HT$_3$ Receptor

Racemic norcisapride, racemic cisapride and their (+)- and (−)-stereoisomers are tested (Cerep, Celle l'Evescault, France) for binding to 5-HT$_3$ receptor subtypes derived from N1E-115 cells.

Following incubation with the appropriate ligands, the preparations are rapidly filtered under vacuum through GF/B glass fiber filters and washed with ice-cold buffer using a Brandel or Packard cell harvester. Bound radioactivity is determined with a liquid scintillation counter (LS 6000, Beckman) using a liquid scintillation cocktail (Formula 989).

Specific radioligand binding to the receptor is defined as the difference between total binding and nonspecific binding determined in the presence of an excess of unlabeled ligand. Results are expressed as a percent inhibition of specific binding obtained in the presence of the compounds. IC$_{50}$ are determined using concentrations ranging from $3 \times 10^{-10}$ M to $10^{-5}$ M to obtain full competition curves and are calculated by non-linear regression analysis. The results are shown in Tables 3 and 4 below.

5-HT$_4$ Receptor

Racemic norcisapride, racemic cisapride and their (+)- and (−)- stereoisomers are tested (Cerep, Celle l'Evescault, France) for binding to 5-HT$_4$ receptor subtypes derived from guinea-pig striata.

Following incubation with the appropriate ligands, the preparations are rapidly filtered under vacuum through GF/B glass fiber filters and washed with ice-cold buffer using a Brandel or Packard cell harvester. Bound radioactivity is determined with a liquid scintillation counter (LS 6000, Beckman) using a liquid scintillation cocktail (Formula 989).

Specific radioligand binding to the receptor is defined as the difference between total binding and nonspecific binding determined in the presence of an excess of unlabeled ligand. Results are expressed as a percent inhibition of specific binding obtained in the presence of the compounds. IC$_{50}$ are determined using concentrations ranging from $3 \times 10^{-10}$ M to $10^{-5}$ M to obtain full competition curves and are calculated by non-linear regression analysis. The results are shown in Tables 3 and 4 below.

TABLE 3

IC$_{50}$ (nM) Values for Binding to 5-HT$_3$ and 5-HT$_4$ Sites

| Compound | 5-HT$_3$ | 5-HT$_4$ | 5-HT$_3$/5-HT$_4$ Ratio |
| --- | --- | --- | --- |
| (±) Norcisapride | 8.2 | 686 | 0.012 |
| (+) Norcisapride | 4.5 | 331 | 0.014 |
| (−) Norcisapride | 30.4 | 1350 | 0.023 |

TABLE 4

IC$_{50}$ (nM) Values for Binding to 5-HT$_3$ and 5-HT$_4$ Sites

| Compound | 5-HT$_3$ | 5-HT$_4$ | 5-HT$_3$/5-HT$_4$ Ratio |
| --- | --- | --- | --- |
| (±) Cisapride | 365 | 169 | 2.2 |
| (+) Cisapride | 310 | 340 | 0.9 |
| (−) Cisapride | 2790 | 199 | 14.0 |

Agonist activity at 5-HT$_4$ receptor sites may also be assessed using an assay based on the ability of active compounds to increase cyclic AMP production in mouse embryo colloculi neurones grown in tissue culture, such as in Dumuis et al., *N. S. Arch. Pharmacol.*, 340:403–410 (1989).

Example 4
Oral Formulation

Tablets

Quantity per Tablet in mg.

| Formula | A | B | C |
|---|---|---|---|
| Active Ingredient (−) Norcisapride | 5.0 | 10.0 | 25.0 |
| Lactose BP | 62.0 | 57.0 | 42.0 |
| Starch BP | 20.0 | 20.0 | 20.0 |
| Microcystalline Cellulose | 10.0 | 10.0 | 10.0 |
| Hydrogenated Vegetable Oil | 1.5 | 1.5 | 1.5 |
| Polyvinylpyrrolidinone | 1.5 | 1.5 | 1.5 |
| Compression Weight | 100.0 | 100.0 | 100.0 |

The active ingredient, (−) norcisapride, is sieved through a suitable sieve and blended with the lactose until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

Example 5
Oral Formulation

Tablets

Quantity per Tablet in mg.

| Formula | A | B | C |
|---|---|---|---|
| Active Ingredient (−) Norcisapride | 5.0 | 10.0 | 25.0 |
| Lactose BP | 48.5 | 43.5 | 28.5 |
| Starch BP | 30.0 | 30.0 | 30.0 |
| Pregelatinized Maize Starch BP | 15.0 | 15.0 | 15.0 |
| Magnesium Stearate BP | 1.5 | 1.5 | 1.5 |
| Compression Weight | 100.0 | 100.0 | 100.0 |

The active ingredient, (−) norcisapride, is sieved through a suitable sieve and blended with lactose, starch, and pregelatinized maize starch until a uniform blend is formed. Suitable volumes of water are added and the powders are granulated. After drying, the granules are then screened and blended with the remaining excipients. The resulting granules are then compressed into tablets of desired shape. Tablets of other strengths may be prepared by altering the ratio of active ingredient to the excipient(s) or the compression weight.

Example 6
Oral Formulation

Capsules

Quantity per Capsule in mg.

| Formula | A | B | C |
|---|---|---|---|
| Active Ingredient (−) Norcisapride | 5.0 | 10.0 | 25.0 |
| Starch 1500 | 94.0 | 89.0 | 74.0 |
| Magnesium Stearate BP | 1.0 | 1.0 | 1.0 |
| Total Weight | 100.0 | 100.0 | 100.0 |

The active ingredient is sieved and blended with the excipients. The mix is filled into size No. 2 hard gelatin capsules using suitable machinery. Other doses may be prepared by altering the fill weight, and if necessary, changing the capsule size to suit.

Example 7

INTRAVENOUS FORMULATION

| Formula | |
|---|---|
| Active Ingredient (−) norcisapride | 1000 µg/mL |
| Dilute Hydrochloric Acid BP | to pH 3.5 |
| Sodium Chloride Injection BP | 1 mL |

The active ingredient is dissolved in dilute hydrochloric acid BP to form a solution having a concentration of 1000 µg/mL (−) norcisapride. The solution is then mixed with sodium chloride injection BP prior to use.

While the present invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating bulimia in a patient which comprises administering to said patient in need of said treatment a therapeutically effective amount of (−) norcisapride, or a pharmaceutically acceptable salt thereof, substantially free of its (+) stereoisomer.

2. The method of claim 1, wherein the patient is a human.

3. The method of claim 1, wherein (−) norcisapride is administered orally.

4. The method of claim 3, wherein (−) norcisapride is administered as a tablet or a capsule.

5. The method of claim 1, wherein the amount administered is from about 0.5 mg to about 500 mg.

6. The method of claim 5, wherein the amount administered is from about 1 mg to about 250 mg.

7. The method of claim 1, wherein (−) norcisapride is administered together with a pharmaceutically acceptable carrier.

8. The method of claim 3, wherein said (−) norcisapride is administered from one to four times per day.

9. The method of claim 1, wherein (−) norcisapride is administered parenterally, transdermally, rectally or sublingually.

10. A method of preventing or managing bulimia in a patient which comprises administering to said patient in need of said prevention or management a therapeutically effective amount of (−) norcisapride, or a pharmaceutically acceptable salt thereof, substantially free of its (−) stereoisomer.

* * * * *